United States Patent [19]
Guthery

[11] Patent Number: 6,110,908
[45] Date of Patent: Aug. 29, 2000

[54] FAST ACTING AND PERSISTENT TOPICAL ANTISEPTIC

[76] Inventor: B. Eugene Guthery, 111 N. Lukfata, Broken Bow, Okla. 74728

[21] Appl. No.: 08/842,471

[22] Filed: May 5, 1997

Related U.S. Application Data

[63] Continuation of application No. 08/412,327, Mar. 31, 1995, abandoned.

[51] Int. Cl.[7] .............................. A01N 55/02; A01N 37/00
[52] U.S. Cl. .......................... 514/188; 514/558; 514/560; 514/513
[58] Field of Search ..................................... 514/188, 558, 514/560, 513

[56] References Cited

PUBLICATIONS

Muh index 10 Ed 1984 #'s 9154, 7892, 3545.
Oelund et al 120: CA; 38156q 1994.
Donat. Pedemont. et al 117 CA:55968m 1992.
Yassum Reslaih 104 CA:230454 w 1986.

*Primary Examiner*—Russell Travers
*Attorney, Agent, or Firm*—Sidley & Austin

[57] ABSTRACT

Stable antiseptic compositions having broad spectrum, fast acting, and profound persistent effect without significant irritation of the tissue to which they are applied are disclosed. The broad spectrum, fast acting component of the present invention comprises one or more antimicrobial alcohols, antimicrobial lipids, or mixtures thereof. The persistent component of the present invention comprises one or more antimicrobial lipids, pyridine-containing compounds, nitrogen-containing antibitics, preservatives, or mixtures thereof, which preferably bind to either or both of the skin surface and intracellular structures within the epidermis. Additional components include antioxidants, emulsifying agents, acidifiers, thickeners, and coloring and texturing compounds. Preferred antiseptic formulations comprise an antimicrobial alcohol such as 70% n-propanol, an antimicrobial lipid such as free fatty acids and/or fatty acid esters, and zinc omadine.

22 Claims, No Drawings

FAST ACTING AND PERSISTENT TOPICAL ANTISEPTIC

CROSS REFERENCE TO RELATED APPLICATION

This is a continuation of U.S. application Ser. No. 08/412,327 filed Mar. 31, 1995 now abandoned.

TECHNICAL FIELD

This invention relates to topical antiseptic compositions.

BACKGROUND OF THE INVENTION

Ever since Maimonides advocated hand washing in the 11th century, surgeons have been seeking better ways of cleaning skin. In the 16th century, the postulate that germs (seminaria) provoked infection was set forth by Fracastoro. Historically, hand-washing for antiseptic purposes had its beginning about 150 years ago by a Hungarian physician, Ignaz Semmelweiss. He is credited with discovering how antiseptic technology can reduce patient mortality from hand-borne infectious agents. Most of the medical community in the 1800's was resistant to theories of antisepsis. In the post-Semmelweiss period, efforts to cleanse skin appear to have been concentrated on the skin of the physician or surgeon. It was not until after Lister and into the twentieth century that serious consideration was given as well to preparation of the patient's skin about to be breached by scalpel. For a review of antiseptics applied to the skin in the twentieth century, see Laufman, H., "Current use of skin and wound cleansers and antiseptics," *The Am J Surgery*, 157:359 (1989).

Antisepsis is the application of microbiocidal antimicrobial chemicals to skin in order to reduce the risk of infection. The microbial flora of the skin can be subdivided into two general groups: (1) transient and (2) resident organisms. An antiseptic is intended to kill both the transient and resident flora of the skin. One hopes to reduce each of these categories of organisms to the maximum extent possible. Transient flora are organisms isolated from the skin, but not demonstrated to be consistently present in the majority of persons. Such flora generally are considered to be transient but are of concern because it can readily be transmitted on hands unless removed by application of an antiseptic. Resident flora are organisms persistently isolated from the skin of most persons. These organisms are considered to be permanent residents of the skin and are not readily removed by mechanical friction or conventional antiseptics. The resident flora reside in sweat ducts, hair ducts, and within the stratum corneum up to more than 25 cell layers deep, however, the majority of the resident bacteria are found in the outer 0.3 mm of the skin.

After recognizing the need for more effective antiseptics, the United States Food and Drug Administration (FDA) developed performance standards for new and novel antiseptics which were published in the *Federal Register* 39:33103–33141 (Sep. 13, 1974). These performance standards required a surgical hand scrub to be broad spectrum, fast acting, and persistent, and a health care personnel hand wash to be broad spectrum, fast acting and, if possible, persistent. In the most recent rulings presented in the *Federal Register* 59:31402–31452 (Jun. 17, 1994), the same performance standards were upheld by the FDA, and testing procedures were given by which new antiseptics were to be comparatively tested against previously approved products.

The term broad spectrum is defined on Page 31422 of the *Federal Register* 59:31402–31452 (Jun. 17, 1994) as having antimicrobial activity against a variety of gram positive and gram negative bacteria, and yeasts.

A patient preoperative skin antiseptic preparation is required to be "a safe, fast-acting broad-spectrum antimicrobial-containing preparation which significantly reduces the number of microorganisms on intact skin." It is further defined as "effective against all types of organisms comprising skin microflora so as to obtain as low a number of microorganisms as possible in a short period of time without injury to the operative site." *Federal Register* 39:33114 (Sep. 13, 1974) Fast acting antiseptics are measured by significant log reduction determined by cultures obtained a few moments following application of the antiseptic.

The quality of persistence, or substantivity, refers to the ability of an antiseptic to continue to kill once it is applied. Substantivity is defined on Page 33110 of the *Federal Register* 39:33103–33141 (Sep. 13, 1974) as the retention or binding of the chemical in the stratum corneum of the skin after rinsing. According to the FDA, "a property [of an antiseptic] such as persistence, which acts to prevent the growth or establishment of transient microorganisms as part of the normal baseline or resident flora, would be an added benefit." *Federal Register* 59:31407 (Jun. 17, 1994). The degree of persistence is measured by the length of time required for the microflora to be fully restored to the baseline microbial count following the use of an antiseptic.

Currently there are several conventional antiseptics that are effective within twenty seconds against transient microorganisms which cause mammalian infection, e.g., 2% aqueous iodine, 70% ethanol, povidone-iodine, chlorhexidine acetate in 70% ethanol, and 2% tincture of iodine. This rapid antibacterial effect demonstrates their efficacy against the transient flora. However, rapid repopulation of bacteria from resident flora occurs with each of these antiseptic treatments. Thus, the FDA has approved use of antiseptics that are effective in reducing the number of transient organisms only on the surface of the skin but are less effective against resident flora within the stratum corneum.

Persistence has remained an elusive goal of antiseptic technology. Although persistence has been required by the FDA since 1974, it has only been achieved moderately with a single product, chlorhexidine gluconate. Only after repeated, daily applications, chlorhexidine has demonstrated antiseptic activity for about six hours. Larson, E., "APIC guidelines for infection control practice," *Am J Infection Control* 16:253–66 (1988). Thus, development of new and novel products that achieve far greater persistence with a single application than repeated applications of chlorhexidine gluconate would be a great improvement for infection control and would meet the standards that the FDA has promulgated since 1974.

As it is desirable to maintain medical procedures as free of microorganisms as possible, it is desirable to have persistence associated with an antiseptic that maintains the microorganism count at as low a level as possible and for as long as possible. This is especially true when an operation lasts for many hours. It is important to minimize the microorganism count of both the operative site and the hands of the surgeon for as long as possible. Persistence is also needed for antiseptics used around a chronic indwelling device such as central catheter, arterial line, or chest tube and for antiseptic treatment of hands of medical personnel in hospitals. Conventional antiseptics produce a rapid antimicrobial effect only on the transient flora and fail to exert a significant reduction of resident flora which may lead to infection with a very significant increase in morbidity and mortality. For example, in 1985, greater than $5–10 billion were spent to treat wound infections in American hospitals. (Wenzel, R. P., *Am J Med* 78(Supp 6B):3–7 (1985)). Consequently, there is a continuing need to improve antiseptics to provide simultaneous broad spectrum, fast acting activity, and persistent activity.

Novel antiseptics have now been found which are very broad spectrum, having antimicrobial activity against vegetative bacteria, yeasts, molds, and viruses, fast acting, and very persistent. Persistence is obtained with a single application. Cumulative persistence, greater than that achieved with alcoholic chlorhexidine gluconate, is obtained with daily use. These products are non-irritating and have reasonably pleasant characteristics associated with the senses of the persons using the antiseptic such as having a pleasant smell and a good tactile feel when applied to the skin. These antiseptics are easily modified to be used over a broad range of uses such as a topical antiseptic applied to the skin of humans or other mammals; a skin preparation antiseptic for use prior to medical operations or procedures; a hand wash for physicians and other medical personnel; a routine antiseptic handwash; an antiseptic at medical appliance invasive sites where needles, catheters, or tubes are placed within the skin or open wounds; a microorganism barrier or an antiseptic within various orifices such as the ear or vagina; an antiseptic to be utilized on sensitive membranes such as mucous membranes, eyes or genitalia; an antiseptic to be used in the treatment of inflammatory dermatoses, e.g., acne, athlete's foot, psoriasis and fungal infections; and an antiseptic treatment for use on animals to prevent infection, e.g., as a treatment against bovine mastitis.

SUMMARY OF THE INVENTION

According to the present invention, new antiseptic formulations for topical application are provided as stable, non-irritating solutions or emulsions effective for broad spectrum, fast acting, and persistent activity for greater than six hours. These formulations each contain at least one broad spectrum, fast acting antimicrobial agent effective for decreasing the number of transient organisms, in combination with at least one persistent agent effective for decreasing the number of resident organisms to achieve persistence.

Broad spectrum and fast acting activity is achieved with alcohols of two to five carbons, which are well known in the art. Since the alcohols are not persistent, the alcohol must be mixed with either zinc omadine (bispyrithione, zinc pyrithione) (OLIN Corporation, Stamford, Conn.) and/or antimicrobial lipids to achieve persistence. Antimicrobial lipids, especially free fatty acids and fatty acid esters, also contribute to the broad spectrum and fast acting activity.

In one aspect of the present invention, the lipid is an antimicrobial free fatty acid, preferably having a chain length of from 2 to about 20 carbons, and most preferable, linoleic (C 18:2) or linolenic acid (C 18:3). In another aspect, the lipid is an antimicrobial fatty acid ester, preferably having a chain length of from 2 to about 24 carbons, and most preferable, glycerol monolaurate.

While some persistence is achieved with antimicrobial fatty acids, the preferred ingredient contributing to persistence is zinc omadine. The persistent agent may also be a preservative such as esters of parahydroxybenzoic acid and aromatic alcohols such as benzyl alcohol and phenylethyl alcohol. Neomycin, an antibiotic, may be added to formulations used around a chronic indwelling device and in treatment of neonates, where percutaneous absorption of zinc omadine is to be avoided.

In one embodiment of the present invention, the topical antiseptic formulation comprises an antimicrobial alcohol, glycol or combination thereof, an antimicrobial lipid, zinc omadine, an emulsifying agent, an acidifier, a thickener, and water. Preferred alcohols are ethanol, n-propanol, isopropanol, and phenylethyl alcohol. A preferred glycol is propylene glycol. The preferred antimicrobial lipids are free fatty acids, fatty acid esters, or mixtures thereof. The zinc omadine, which is poorly soluble in alcohols or water, is suspended by emulsifying agents and thickeners.

A preferred embodiment comprises from about 30% to about 98%. (v/v) alcohol, glycol, or mixture thereof, from about 0.0001% to about 15% (w/v) zinc omadine; from about 3 to about 12% emulsifying agent; from about 1 to 2% acidifier, and from about 0.25 to 1% thickener. A most preferred embodiment comprises about 70% (v/v) alcohol, glycol, or mixture thereof; from about 1 to about 5% antimicrobial lipid; from about 1 to about 2% (w/v) zinc omadine; from about 1.5 to about 12% emulsifying agent; from about 1 to about 2% acidifier, and about 0.25 to about 1% thickeners. The preferred pH range is between 2 and 5; and most preferred, between 3 and 4.

In another embodiment of the present invention, the topical antiseptic formulation comprises alcohol, iodine, and an antimicrobial lipid. The preferred alcohols are ethyl, isopropanol, and n-propanol. The antimicrobial lipids of choice are long-chain unsaturated fatty acids such as linoleic or linolenic fatty acids. The most preferred embodiment comprises about 70% (v/v) alcohol, from about 1 to 2% iodine, and from about 1 to 2% antimicrobial fatty acids.

In another embodiment of the invention, the fatty acids and zinc omadine are incorporated into a cream base. In this instance the fast acting, broad spectrum activity is mainly provided by the antimicrobial fatty acids, glycerol monolaurate, or mixture thereof, and the persistence is mainly from zinc omadine. The preferred embodiment comprises about 2 to 10% antimicrobial lipids and from about 1 to 2% zinc omadine. Over-the-counter products such as those published in the *Federal Register* or prescription products may be added to the cream base.

DETAILED DESCRIPTION

The present invention is directed to a topical antiseptic that advantageously provides broad spectrum and fast acting antimicrobial action against existing microorganisms on the surface of living tissue and persistence in preventing recolonization of the treated surface. In addition to the broad spectrum and fast acting antimicrobial components and persistent components of the present invention, the antiseptic compositions may also contain chelating agents, antioxidants, emulsifiers, colorings, texturings, thickeners, pH adjusting agents, over-the counter (OTC) treatments, or prescription compounds.

It is preferred to have an antiseptic that not only quickly kills microorganisms with a high log ratio kill on contact with the skin, but also has the ability to: 1) penetrate throughout the levels of the skin where microorganisms reside, 2) bind to lipids or proteins in the intercellular layers of the epidermis to produce a prolonged kill or persistence, and 3) bind to lipids or proteins on the surface of the skin so as to have a prolonged or persistent kill where organisms are killed as they attempt to recolonize the skin surface from their resident sources.

In particular, the antiseptic compositions of the present invention comprise a broad spectrum, fast acting antimicrobial component(s) and a persistent component(s).

The broad spectrum, fast acting component of the antiseptic composition of the present invention preferably comprises an aliphatic alcohol, e.g., ethyl, isopropyl, n-propyl, butyl, and amyl alcohols or mixtures thereof in concentrations above 50%. Higher chain length alcohols such as n-decanol may also be used, especially in mixtures with lower chain alcohols, since these alcohols have slower evaporation rates and enhance penetration into the stratum corneum. Preferred concentrations for higher chain length alcohols are about 2 to about 25% (v/v). Aromatic alcohols may also be utilized advantageously in conjunction with aliphatic alcohols. The preferred aromatic alcohols include phenylethyl alcohol, benzyl alcohol, and phenoxyethyl alcohol in concentrations of about 0.25 to about 4% (v/v). Total alcohol concentrations of 50 to 75% (v/v) are most effective against microorganisms of interest.

Antimicrobial lipids are known bacteriostatic agents which act synergistically with alcohol(s) to achieve broad spectrum, fast acting antimicrobial activity. It is disclosed herein for the first time that free fatty acids demonstrate persistent antimicrobial activity on human skin resident flora. Preferable antimicrobial lipids or lipid-like materials include: fatty acids; fatty acid dimers, trimers, or tetramer acids; fatty acid esters; phospholipids; and glycosphingolipids. It is noted that the preferred lipid materials of the present invention for use as the persistent component are naturally occurring materials within the human skin: free fatty acids, phospholipids, and glycosphingolipids. The antimicrobial lipid(s) contribute to both the broad spectrum, fast acting antimicrobial aspect and the persistence aspect of the present invention.

In particular, the antimicrobial lipid component is preferably a free fatty acid. The antimicrobial free fatty acid may be saturated or unsaturated, straight or branched with chain lengths of two to thirty carbons. A preferred saturated fatty acid is C12, or lauric acid. Preferred antimicrobial unsaturated fatty acids are linolenic and linoleic acids. Linoleic and linolenic fatty acids are readily available as hydrolysates of various oils, such as linseed oil. These are provided in commercial products such as Emery 305 or 315 for linoleic fatty acid, Emery 644 a commercially-available mixture of saturated and unsaturated free fatty acids with chain lengths ranging from C16 to C18, specifically about 54% linolenic acid, about 20% oleic acid, about 14% linoleic acid, about 8% palmitic acid, and about 4% stearic acid, and Emery 658, a commercially available mixture of saturated fatty acids with chain lengths ranging from C6 to C12, specifically about 58% caprylic acid, about 40% capric acid, about 1% caproic acid, and about 1% lauric acid (Henkel Corporation, Emery Group, Cincinnati, Ohio). GLA-70 is a hydrolysate concentrate from evening primrose oil containing the free fatty acid gamma-dihomolinolenic acid which is preferred for inflamed skin. Other sources of free fatty acids are hydrolysates of coconut oil, corn oil, soybean oil, borage oil, safflower oil, sunflower oil, sesame seed oil, and wheat germ oil.

Antimicrobial fatty acid esters of the present invention may be: 1) monoglycerol esters of fatty acids with carbon chain lengths from two to twenty-four; 2) methyl esters of fatty acids including alpha-hydroxymethyl esters; 3) polyglycerol esters with carbon chain lengths from two to twenty-four, saturated or unsaturated, straight or branched; 4) sucrose esters of fatty acids including cis and trans isomers; or (5) di- and triglycerol esters with carbon chain lengths from two to twenty-four. The preferred fatty acid ester is glycerol monolaurate, which has high antimicrobial activity against skin organisms.

The fatty acids and fatty acid esters increase in antimicrobial activity as the pH of the composition decreases. Typically, as the pH of a solution containing the fatty acids decreases and/or as the chain length of the fatty acid increases, the antimicrobicidal activity of the fatty acid also increases. The activity of the fatty acids and fatty acid esters increases dramatically if the component used to lower the pH is also a calcium or magnesium chelator. Preferred calcium and magnesium chelators are citric acid, phosphoric acid, phosphonic acids and polyphosphoric acids to lower the pH to less than 4. The pH cannot be lower than 2, however, without producing ester formation of the free fatty acids with the corresponding alcohol or hydrolysis of glycerol monolaurate.

For the best activity, it is mandatory for the fatty acids to be free fatty acids in solution. Surfactants may impair the antimicrobial activity of lipids. When antimicrobial free fatty acids are used with alcohols, the broad spectrum, fast acting antimicrobial activity obtained with the alcohol-free fatty acid combination is synergistic. Alcohols or glycols typically are good solvents for the free fatty acids and fatty acid esters. Iodine may be added to the solution of alcohol and antimicrobial lipid to provide additional broad spectrum, fast acting antimicrobial activity.

The preferred fast acting antimicrobial components of the present invention for intact skin include medium-chain (12 carbons) saturated fatty acid monoesters and long-chain (18 carbons) unsaturated free fatty acids. The preferred range of the medium-chain fatty acid esters is from about 0.001% to 7% by weight; and more preferred, from about 1% to about 3% by weight. The preferred medium-chain fatty acid monoester is glycerol monolaurate (Lauricidin). The range for the unsaturated fatty acid is from about 0.0001% to about 30% by weight; the preferred range is from about 0.01% to about 10% by weight; and the most preferred range is from about 1% to about 5% by weight.

Other preferred lipids of the present invention are phospholipids such as lysolecithin, phosphatidylcholine, phosphatidylethanolamine, phosphatidylserine, phosphatidylinositol, and phosphatidyl-N-acylethanolamine. It is also foreseen that glycosphingolipids, especially those enriched in n-acyl-alpha-hydroxyacids could be used. Other components with long alkyl groups with a lipophilic, hydrophobic end are foreseen as useable. This would include long-chain alcohols, saturated or unsaturated, straight or branched; medium to long-chain aldehydes, saturated or unsaturated.

In conjunction with the broad spectrum, fast acting alcohol(s) and persistent antimicrobial lipid components, the present invention may also comprise additional persistent component(s) to achieve persistence of greater than 6 hours and routinely over 24 hours. Other persistent components which may be added to the antiseptic composition of the present invention include zinc omadine, nitrogen-containing antibiotics, and preservatives.

Prolonged persistence is achieved with bispyrithiones. Zinc pyrithione, or zinc omadine, is preferred. Zinc omadine is not easily absorbed through intact epidermis or mucous membranes, but is soluble in sebum and penetrates into hair follicles where resident flora reside. The antimicrobial spectrum of zinc omadine includes vegetative bacteria, molds, and yeasts. It is disclosed herein for the first time that zinc omadine demonstrates persistent antimicrobial activity on human skin.

When magnesium pyrithione was added to the alcohol-antimicrobial lipid combination of the present invention, it was found that it could not readily be used, because an insoluble precipitate formed that reduced the antimicrobial activity of the pyrithione and the antimicrobial lipid. Because zinc omadine is practically insoluble in alcohol and water and incompatible with free fatty acids, it appeared that incorporation of zinc omadine into the alcohol-antimicrobial lipid combination in the present invention would not be achievable. However, when appropriate amounts of ethoxylated cetyl and stearyl alcohol emulsifying agents sold under the trade name Polawax (Croda, Inc., Parsippany, N.J.) were added to the alcohol-antimicrobial lipid antiseptic, a stable emulsion was formed into which the previously insoluble zinc omadine was readily incorporated and did not precipitate over time. In lotion or cream formulations containing emulsifiers of ethoxylated cetyl and stearyl alcohols and/or glyceryl monostearate, zinc omadine can be added to antiseptics containing long-chain alcohols, long-chain unsaturated fatty acids, medium-chain saturated fatty acids, and/or their esters. Zinc omadine can be incorporated at a concentration of from about 0.00010% to about 5.0% (w/v), more preferably in a range of from about 0.5% to about 4.0% (w/v), and most preferably in a range of from about 1.0% to about 2.0% (w/v).

Certain preservatives may be added to the antiseptic composition as highly effective fast acting and/or persistent components. These include preservatives that are conventionally utilized in the cosmetics industry: parabens (alkyl esters of parahydroxy-benzoic acid such as methyl-, ethyl-, propyl-, butyl- and benzyl-p-hydroxy benzoates); aromatic alcohols such as benzyl alcohol and phenyl-ethyl alcohol.

Another group of fast acting antimicrobial and persistent compounds which could be used in the present invention are antibiotics such as neomycin. Neomycin can be incorporated into the broad spectrum, fast acting, and persistent alcohol-antimicrobial lipid-zinc omadine antiseptic for use around chronic indwelling devices in adolescents and adults. When neomycin is combined with alcohols and antimicrobial lipids, it is foreseen that this combination would be especially effective as a substitute for zinc omadine in neonates through adolescents where percutaneous absorption of zinc omadine could be deleterious.

It is also preferred to incorporate an antioxidant component into the compositions of the present invention to prevent saturation of the unsaturated fatty acids. Suitable antioxidants include betahydroxytoluene, Vitamin E, Vitamin C, alpha-tocopherol, and propyl gallate. A preferred antioxidant is propyl gallate or mixtures containing propyl gallate such as Tenox PG or Tenox 51 (Eastman Chemical Co., Kingsport, Tenn.). Preferably, propyl gallate is used in concentrations of about 0.1 to about 2.0%. Tenox is used in concentrations of about 0.1 to about 10%.

A thickener may also be utilized for certain embodiments of the present invention to decrease the quick evaporation of alcohols and to keep various low viscosity fluids from quickly running off of the surface being treated. A preferable thickener has been found to be hydroxypropyl cellulose sold under the trademark Klucel HFNF 1500-3000 by Aqualon, Wilmington, Del. In preparing the antiseptics of the present invention, the alcohol and Klucel are preferably mixed overnight with gentle stirring to fully hydrate the Klucel. Also, care must be taken while adjusting the pH of the antiseptics, because at a pH of less than 2, hydrolysis of Klucel can occur.

The antiseptic compositions of the present invention may also be combined with conventional over-the-counter (OTC) or prescription ingredients to achieve salutary effects. For the treatment of viruses, 2-deoxy-D-glucose or zinc sulfate may be added to increase the antiviral activity of the antiseptic. Improved kill of microorganisms is also found if a chelating agent component is incorporated. Preferably, the chelating agent is a magnesium or calcium chelator that also tends to lower the pH of the composition. Suitable chelating agents of this type are polyphosphoric acid, citric acid, phosphonic acids, and phosphoric acids.

Broad spectrum, fast acting alcohols and antimicrobial lipids tend to increase in antimicrobial action at an acidic pH. Further, the emulsion with zinc omadine requires an acidic pH of greater than 2 but less than 4 to be stable. Therefore, the pH of the final antiseptic must be adjusted. The following pH levels are preferred in the present invention: for intact skin, pH 4 or less, preferably from about 2 to about 3.5. Since other ingredients added to the composition of the present invention may modify the pH, the pH of the overall composition should be adjusted subsequent to addition of all of the components. For example, the solution may be adjusted with a phosphoric acid/monobasic sodium phosphate buffer, glacial acetic acid/sodium acetate buffer, citric acid/sodium citrate buffer, or combinations of organophosphonates such as Dequest 2010, 2060, and 2016 (Monsanto Company, St. Louis, Mo.).

Antiseptic compositions of the present invention have been formulated to provide the following advantages: 1) broad spectrum; 2) fast acting; 3) persistent, both by maintaining a low quantity of microorganisms on tissue treated by the composition for a substantial period of time and not allowing the level of microorganisms on or in the tissue to return to normal for a period of time; 4) not irritating to the skin of humans and other mammals; adapted to penetrate and bind into the epidermis and kill microorganisms therein; user-friendly, having odor, tactile qualities and other characteristics which are pleasant to those both applying and receiving the compositions; adaptable or modifiable to a wide range of medical uses as antiseptics; and relatively easy to prepare, stable in shipment and especially effective for their intended purposes.

Other objects and advantages of this invention will become apparent from the following descriptions wherein are set forth, by way of illustration and example, certain embodiments of this invention. It is to be understood that while certain forms of the present invention have been illustrated and described herein, it is not to be limited to the specific forms or arrangement of parts described and shown.

EXAMPLE 1

Preparation of a Minimum Requirement Antiseptic without Fatty Acids

To prepare the antiseptic as indicated in Table I, initially mix approximately 95% of the volume of n-propanol with the thickening agent Klucel. To hydrate the Klucel, stir for 2–3 hours with equipment that produces high shear, or overnight with equipment that only produces low shear. Add the additional 5% of n-propanol, and while continuously stirring, add the appropriate amount of the emulsifier. Adjust the pH as required, add the appropriate amount of zinc omadine, and q.s. to 100% with deionized water.

EXAMPLE 2

Preparation of Minimum Requirement Antiseptic with Antimicrobial Lipid

To formulate an antiseptic containing fatty acids, the ingredients given in Table II, initially mix approximately 95% of the volume of n-propanol with the thickening agent Klucel. To hydrate the Klucel, stir for 2–3 hours with equipment that produces high shear, or overnight with equipment that only produces low shear. Add the additional 5% of n-propanol, and while continuously stirring, add the appropriate amount of the emulsifier, antimicrobial lipid, and antioxidant. Adjust the pH as required,
add the appropriate amount of zinc omadine, and q.s. to 100% with deionized water.

TABLE I

EXEMPLARY FORMULATION FOR MINIMUM REQUIREMENT ANTISEPTIC

| COMPONENT | CONCENTRATION (%) |
|---|---|
| BROAD SPECTRUM FAST ACTING ALCOHOL | |
| N-Propanol[a] | 70 |
| EMULSIFIER | |
| Polawax[b] | 6 |
| PRESERVATIVE | |
| Zinc omadine[b,c] | 2 |
| THICKENING AGENT | |
| Klucel[b] | 1 |
| pH ADJUSTING AGENT | |
| Phosphoric acid[b] | 2 |

[a]Concentration in percent (v/v).
[b]Concentration in percent (w/v).
[c]Quick-kill and persistent agent.

EXAMPLE 3

In vitro Measurement of Antimicrobial Activity of Zinc Omadine and Other Potential Components of New Antiseptic Formulations Seven compounds or mixtures were tested including zinc omadine, two free fatty acid hydrolysates (Emery 315 and Emery 644), acetic acid, propylene glycol, and two antiseptic formulations that contained 2.5% zinc omadine and 3.0% fatty
acids, with or without 0.25% Klucel (AS+K and AS−K, respectively). The pH of the antiseptic mixtures was 2.7–2.8.

TABLE II

EXEMPLARY FORMULATION FOR MINIMUM REQUIREMENT ANTISEPTIC

| COMPONENT | CONCENTRATION (%) |
|---|---|
| BROAD SPECTRUM FAST ACTING ALCOHOL | |
| N-Propanol[a] | 70 |
| EMULSIFIER | |
| Polawax[b] | 6 |
| ANTIMICROBIAL LIPID | |
| Emery 305[b] | 5 |
| PERSISTENT AGENT | |
| Zinc omadine[b,c] | 2 |
| THICKENING AGENT | |
| Klucel[b] | 1 |

TABLE II-continued

EXEMPLARY FORMULATION FOR MINIMUM REQUIREMENT ANTISEPTIC

| COMPONENT | CONCENTRATION (%) |
|---|---|
| pH ADJUSTING AGENT | |
| Phosphoric acid[b] | 2 |
| ANTIOXIDANT | |
| Propyl gallate[b] | 0.1 |

[a]Concentration in percent (v/v).
[b]Concentration in percent (w/v).
[c]Quick-kill and persistent agent.

Over 200 bacterial and fungal isolates from clinical patient infections at the University of Iowa Hospitals and Clinics (Iowa City, Iowa) were used to determine antimicrobial activity. Each strain was identified by routine methods (Vitek Systems, API, etc.) in use in the Medical Microbiology Division laboratories. The following species were processed: *Staphylococcus aureus* (10 strains, five resistant to methicillin), coagulase-negative staphylococci (10 strains representing four species, five resistant to methicillin), *Enterococcus* spp. (10 strains), *Streptococcus pyogenes* (10 strains), beta-hemolytic streptococci groups B, C, and G (10 strains), *Corynebacterium jeikeium* (10 strains), *Corynebacterium parvum* (previously *Propionibacterium acnes*) (10 strains), *Escherichia coli* (10 strains representing two species), *Enterobacter* spp. (10 strains), *Klebsiella* spp. (10 strains, representing two species), *Pseudomonas aeruginosa* (10 strains), *Citrobacter* spp. (10 strains), indole-positive Proteeae (10 strains), *Salmonella/Shigella* spp. (10 strains), *Serratia marcescens* (10 strains), *Acinetobacter* spp. (10 strains), *Xanthomonas maltophilia* (10 strains), *Prevotella bivia-disiens* (10 strains), *Bacteroides fragilis* (10 strains), *Gardnerella vaginalis* (10 strains), *Lactobacillus* spp. (10 strains), *Mobiluncus* spp. (10 strains), *Aspergillus* spp. (5 strains), *Candida albicans* (5 strains), *Candida* spp. (5 strains), and dermatophytes (5 strains).

All susceptibility testing was performed by methods conforming to the recommendations of the National Committee for Clinical Laboratory Standards (NCCLS). Mueller-Hinton agar (Difco Laboratories, Detroit, Mich.) was used with supplemental 5% sheep erythrocytes for fastidious species (streptococci, corynebacteria). Dilution schedules were selected based on preliminary pilot studies covering a dilution range of 10% to 0.001% solutions of each compound or mixture. The following dilution ranges were used for each substance/mixture following pilot study experiments: 1) zinc omadine, 0.25% to 0.001%, or 250 to 1 microgram/ml; 2) acetic acid and the two antiseptic mixtures, 4% to 0.015%; and 3) propylene glycol and two fatty acid hydrolysates, Emery 644 and Emersol 305, 16% to 0.25%. Note that the antiseptic solutions and fatty acids were listed as % solutions but actually represent dilutions of the provided formulation(s), e.g. 1:25 to 1:6400.

The pH of the agar medium was 7.2 to 7.4 conforming to the NCCLS recommendations. Therefore, the antimicrobial action of several of these substances which perform maximally at acidic pH ranges was potentially underestimated because of testing at standard microbiology pH levels favoring the growth of pathogenic organisms.

Table III lists the minimum inhibitory concentrations (MICs) obtained in the pilot study in which 10% to 0.001% solutions were tested against laboratory strains of seven bacteria and one yeast. From these results, the assay dilution ranges were selected.

When the antiseptic formulations (2.5% zinc omadine and 3.0% fatty acids in n-propyl alcohol) with and without a thickening agent (0.25% Klucel) were tested as a dilution of the final concentration, excellent inhibition was observed as shown in Table III. All gram positive organisms were inhibited at less than 0.1% dilution, and all gram negative organisms, at less than 1.0% dilution.

Results for seven antimicrobial agents against a wide variety of the clinical bacterial isolates were tabulated as the concentration inhibiting 50% and 90% of the tested organisms and are presented in Table IV. The range of MICs is also listed for each tested substance.

Antimicrobial activities of zinc omadine, fatty acids, and antiseptic plus Klucel were measured using clinical isolates of several microorganisms, including additional gram positive bacteria, vaginosis-associated bacteria, yeasts and molds. Table V presents the results as the concentration inhibiting 50% and 90% of the tested organisms, with the MIC range also provided.

These in vitro susceptibility tests using NCCLS procedures confirm the spectrum and level of potency previously stated by the zinc omadine manufacturer (Olin Chemicals). Zinc omadine has a spectrum of activity inhibiting all significant gram positive pathogens at <0.004%, or <40 micrograms/ml. Similarly, with the exception of Pseudomonas and Xanthomonas spp., all enteric bacilli tested had MICs at <0.004%, or <40 micrograms/ml. *Pseudomonas aeruginosa* and *Xanthomonas maltophilia* had higher MICs at <0.12% (120 micrograms/ml) and 0.15% (150 micrograms/ml), respectively. Aspergillus spp., *Candida albicans*, other Candida spp., and the dermatophytes were inhibited at a zinc omadine concentration of <0.001%, or 10 micrograms/ml.

TABLE III

DILUTION MIC TEST RANGING PILOT STUDY FOR SEVEN ANTIMICROBIAL AGENTS OR MIXTURES AGAINST BACTERIA AND YEAST CONTROL STRAINS

| | MIC in % dilution for various antimicrobial and mixtures[a] | | | | | | |
|---|---|---|---|---|---|---|---|
| Organism | Zinc Omadine | Emery 644 | Emersol 315 | Anti- septic − Klucel | Anti- septic + Klucel | Acetic Acid | Propylene Glycol |
| S. aureus 25923 | 0.001 | 1 | 1 | 0.1 | 0.1 | 1 | >10 |
| S. aureus 29213 | 0.001 | 1 | 1 | 0.1 | 0.1 | 1 | >10 |
| S. epidermidis 7872 | 0.001 | 1 | 1 | 0.1 | 0.1 | 1 | >10 |
| E. faecalis 29212 | 0.001 | 1 | 10 | 0.1 | 0.1 | 1 | 10 |
| E. coli 25922 | 0.01 | 10 | >10 | 0.1 | 0.1 | 1 | 10 |
| P. aeruginosa 27853 | 0.1 | 10 | >10 | 1 | 1 | 1 | 10 |
| C. albicans 8501 | 0.01 | 10 | >10 | 0.01 | 0.01 | 1 | 10 |

[a]Dilution schedule in Log10 intervals of the provided solution (1:100 dilution of acetic acid = 0.36% (w/v) and a 1% solution Zinc Omadine = 1000 µg/ml.

TABLE IV

ANTIMICROBIAL ACTIVITY OF SEVEN AGENTS OR MIXTURES TESTED AGAINST 109 CLINICAL BACTERIAL ISOLATES

| Organism | Antimicrobial | MIC as a % solution[a] | | |
|---|---|---|---|---|
| (No. tested) | Agent | MIC50 | MIC90 | Range |
| GRAM POSITIVE BACTERIA | Zinc omadine | <0.001 | <0.001 | <0.001 |
| S. aureus (10) | Emery 644 | <0.25 | <0.25 | <0.25 |
|  | Emersol 315 | <0.5 | 0.5 | <0.25–0.5 |
|  | AS − K[b] | <0.015 | <0.015 | <0.015 |
|  | AS + K[b] | <0.015 | <0.015 | <0.015 |
|  | Acetic acid | 0.12 | 0.12 | <0.06–0.12 |
|  | Propylene glycol | 16 | 16 | 8–16 |
| Coagulase-negative | Zinc omadine | <0.001 | <0.001 | <0.001–0.002 |
| staphylococcus | Emery 644 | <0.25 | 0.5 | <0.25–0.5 |
| (10)[c] | Emersol 315 | 0.5 | 1 | <0.25–1 |
|  | AS − K | <0.015 | 0.03 | <0.015–0.03 |
|  | AS + K | <0.015 | 0.03 | <0.015–0.06 |
|  | Acetic acid | 0.12 | 0.12 | <0.06–0.12 |
|  | Propylene glycol | 8 | 8 | 4–8 |
| Enterococcus spp. | Zinc omadine | 0.002 | 0.002 | <0.001–0.002 |
| (10)[d] | Emery 644 | 0.5 | 0.5 | <0.25–0.5 |
|  | Emersol 315 | 0.5 | 0.5 | <0.25–0.5 |
|  | AS − K | 0.06 | 0.06 | 0.03–0.06 |
|  | AS + K | 0.06 | 0.06 | 0.03–0.06 |
|  | Acetic acid | 0.12 | 0.12 | 0.12 |
|  | Propylene glycol | 8 | 8 | 8 |
| S. pyogenes (9) | Zinc omadine | 0.002 | 0.002 | <0.001–0.002 |
|  | Emery 644 | 1 | 1 | 0.5–1 |
|  | Emersol 315 | 1 | 1 | 1 |
|  | AS − K | 0.06 | 0.12 | 0.03–0.12 |
|  | AS + K | 0.06 | 0.12 | 0.03–0.12 |
|  | Acetic acid | <0.06 | <0.06 | <0.06 |
|  | Propylene glycol | 16 | 16 | 16 |
| β-haemolytic | Zinc omadine | <0.001 | <0.001 | <0.001 |
| streptococci GR. | Emery 644 | 1 | 1 | 0.5–1 |
| B, C and G (10)[e] | Emersol 315 | 1 | 1 | 1 |
|  | AS − K | 0.03 | 0.03 | 0.03 |
|  | AS + K | 0.03 | 0.03 | <0.015–0.03 |
|  | Acetic acid | 0.12 | 0.12 | 0.12 |
|  | Propylene glycol | 16 | 16 | 16 |
| C. jeikeium (10) | Zinc omadine | 0.002 | 0.002 | 0.002–0.004 |
|  | Emery 644 | 1 | 1 | 0.5–1 |
|  | Emersol 315 | 1 | 1 | 1 |
|  | AS − K | 0.12 | 0.12 | 0.12 |
|  | AS + K | 0.06 | 0.06 | 0.06–0.12 |
|  | Acetic acid | 0.12 | 0.12 | <0.06–0.12 |
|  | Propylene glycol | 8 | 16 | 4–16 |
| C. parvum (10) | Zinc omadine | 0.008 | 0.008 | 0.004–0.008 |
|  | Emery 644 | 1 | 1 | 1 |
|  | Emersol 315 | 2 | 2 | 2 |
|  | AS − K | 0.12 | 0.12 | 0.12–0.25 |
|  | AS + K | 0.12 | 0.25 | 0.12–0.25 |
|  | Acetic acid | 0.12 | 0.12 | 0.12 |
|  | Propylene glycol | 16 | 16 | 16 |
| GRAM-NEGATIVE BACTERIA | Acetic acid | 0.12 | 0.12 | 0.12 |
| E. coli (10) | Propylene glycol | 16 | 16 | 16 |
|  | Zinc omadine | <0.001 | <0.001 | <0.001 |
|  | Emery 644 | 1 | 2 | 1–2 |
|  | Emersol 315 | 16 | 16 | 8–16 |
|  | AS − K | 0.03 | 0.03 | 0.03 |
|  | AS + K | 0.03 | 0.03 | 0.03 |
|  | Acetic acid | <0.06 | <0.06 | <0.06 |
|  | Propylene glycol | 16 | 16 | 16 |
| Enterobacter spp. | Zinc omadine | 0.002 | 0.002 | 0.002 |
| (10)[f] | Emery 644 | 2 | 4 | 2–4 |
|  | Emersol 315 | >16 | >16 | >16 |
|  | AS − K | 0.06 | 0.06 | 0.06 |
|  | AS + K | 0.06 | 0.06 | 0.06–0.12 |
|  | Acetic acid | <0.06 | <0.06 | <0.06 |
|  | Propylene glycol | 16 | 16 | 16 |
| Klebsiella spp. | Zinc omadine | 0.002 | 0.002 | <0.001–0.002 |
| (10)[g] | Emery 644 | 2 | 4 | 2–4 |
|  | Emersol 315 | >16 | >16 | 16–>16 |
|  | AS − K | 0.06 | 0.06 | 0.03–0.12 |
|  | AS + K | 0.06 | 0.06 | 0.03–0.12 |
|  | Acetic acid | <0.06 | <0.06 | <0.06 |

TABLE IV-continued

ANTIMICROBIAL ACTIVITY OF SEVEN AGENTS OR MIXTURES TESTED AGAINST 109 CLINICAL BACTERIAL ISOLATES

| Organism | Antimicrobial | MIC as a % solution[a] | | |
|---|---|---|---|---|
| (No. tested) | Agent | MIC50 | MIC90 | Range |
| | Propylene glycol | 16 | 16 | 16 |
| P. aeruginosa (10) | Zinc omadine | 0.12 | 0.12 | 0.12 |
| | Emery 644 | 2 | 4 | 2–4 |
| | Emersol 315 | 16 | 16 | 8–16 |
| | AS − K | 1 | 1 | 1 |
| | AS + K | 0.5 | 1 | 0.5–1 |
| | Acetic acid | <0.06 | <0.06 | <0.06 |
| | Propylene glycol | 8 | 16 | 8–16 |

[a]Zinc omadine 0.001% solution. Other MICs represent (w/v) calculated % solutions.
[b]AS − K = antiseptic (2.5% zinc omadine, 3% fatty acids in n-propyl alcohol) without Klucel; AS + K = antiseptic with Klucel
[c]Also S. simulans (2 strains).
[d]Includes E. faecalis (5 strains), E. faecium (2 strains), E. avium (1 strain), and E. raffinosus (1 strain).
[e]Includes serogroups B (3 strains), C (1 strain) and G (6 strains).
[f]Includes E. cloacae (7 strains) and E. aerogenes (3 strains).
[g]Includes K. oxytoca (2 strains) and K. pneumoniae (8 strains).

TABLE V

ANTIMICROBIAL ACTIVITY OF THREE AGENTS TESTED AGAINST SEVERAL ADDITIONAL BACTERIAL ISOLATES

| Organism (no tested) | Antimicrobial Agent | MIC as a % solutions[a] | | |
|---|---|---|---|---|
| | | MIC50 | MIC90 | Range |
| GRAM NEGATIVE BACTERIA | Zinc omadine | 0.002 | 0.002 | 0.002–0.004 |
| Citrobacter ssp. | Emery 644 | 2 | 2 | 2 |
| (10)[b] | AS + K[c] | 0.06 | 0.06 | 0.03–0.12 |
| Indole-positive | Zinc omadine | 0.004 | 0.015 | 0.004–0.015 |
| Proteeae (10)[d] | Emery 644 | 2 | 2 | 2 |
| | AS + K | 0.12 | 0.5 | 0.12–0.5 |
| Salmonella/Shigella | Zinc omadine | 0.002 | 0.002 | 0.002 |
| (10)[e] | Emery 644 | 4 | 4 | 2–4 |
| | AS + K | 0.06 | 0.06 | 0.06 |
| S. marcescens (10) | Zinc omadine | 0.004 | 0.004 | 0.002–0.004 |
| | Emery 644 | 4 | 4 | 4 |
| | AS + K | 0.12 | 0.12 | 0.06–0.12 |
| Acinetobacter ssp. | Zinc omadine | 0.004 | 0.015 | <0.001–0.015 |
| (10)[f] | Emery 644 | 1 | 2 | 1–2 |
| | AS + K | 0.25 | 0.5 | 0.03–1 |
| X. maltophilia (10) | Zinc omadine | 0.015 | 0.03 | 0.004–0.03 |
| | Emery 644 | 2 | 4 | 2–4 |
| | AS + K | 0.5 | 1 | 0.12–1 |
| VAGINOSIS-ASSOCIATED BACTERIA | Zinc omadine | <0.001 | <0.001 | <0.001 |
| P. bivia-disiens | Emery 644 | 0.5 | 0.5 | <0.25–1 |
| (10) | AS + K | <0.015 | 0.03 | <0.015–0.03 |
| B. fragilis (10) | Zinc omadine | 0.002 | 0.002 | <0.001–0.002 |
| | Emery 644 | 1 | 1 | 0.5–1 |
| | AS + K | 0.06 | 0.06 | 0.03–0.06 |
| G. vaginalis (10) | Zinc omadine | <0.001 | 0.002 | <0.001–0.002 |
| | Emery 644 | <0.25 | <0.125 | <0.25 |
| | AS + K | 0.06 | 0.06 | <0.015–0.12 |
| Lactobacillus spp. | Zinc omadine | <0.001 | <0.001 | <0.001–0.004 |
| (10) | Emery 644 | 2 | 2 | <0.25–2 |
| | AS + K | <0.015 | <0.015 | <0.015–0.25 |
| Mobiluncus spp. (10) | Zinc omadine | 0.002 | 0.002 | <0.001–0.002 |
| | Emery 644 | <0.25 | <0.25 | <0.25 |
| | AS + K | 0.12 | 0.12 | <0.015–0.12 |
| YEAST and FUNGI | Zinc omadine | <0.001 | | <0.001–0.015 |
| Aspergillus spp. | Emery 644 | >16 | | 4–>16 |
| (5)[g] | AS + K | 1 | | <0.015–1 |
| C. albicans (5) | Zinc omadine | <0.001 | | <0.001 |
| | Emery 644 | >16 | | >16 |
| | AS + K | <0.015 | | <0.015 |
| Candida spp. (5)[h] | Zinc omadine | <0.001 | | <0.001 |
| | Emery 644 | 2 | | 0.05–>16 |

TABLE V-continued

ANTIMICROBIAL ACTIVITY OF THREE AGENTS TESTED AGAINST SEVERAL ADDITIONAL BACTERIAL ISOLATES

| Organism (no tested) | Anti-microbial Agent | MIC as a % solutions[a] | | |
|---|---|---|---|---|
| | | MIC50 | MIC90 | Range |
| Dermatophytes (5)[i] | AS + K | <0.015 | | <0.015 |
| | Zinc omadine | <0.001 | | <0.001 |
| | Emery 644 | 0.5 | | 0.5 |
| | AS + K | <0.015 | | <0.015 |

[a]Zinc omadine 0.001% solution. Other MICs represent (w/v) calculated % solutions.
[b]Includes *C. diversus* (6 strains) and *C. freundii* (4 strains).
[c]AS + K = antiseptic (2.5% zinc omadine and 3% fatty acids in n-propyl alcohol) with Klucel.
[d]Includes *M. morganii* (5 strains) and Providencia spp. (5 strains, 2 species).
[e]Includes *S. enteritidis* (6 strains) and *S. sonnei* (4 strains).
[f]Includes *A. antitratus* (8 strains) and *A. lwoffii* (2 strains).
[g]Includes *A. flavus* (2 strains), *A fumigatus* (2 strains), and *A. terreus* (1 strain).
[h]Includes *C. glabrata* (1 strain), *C. krusei* (1 strain), *C. lusitaniae* (1 strain), *C. parapsilosis* (1 strain), and *C. tropicalis* (1 strain).
[i]Includes one strain each of *M. canis*, *M. gypseum*, *T. mentagrophytes*, *T. rubrum*, and Trichophyton spp.

The fatty acid hydrolysates had a comparable spectrum of activity to that of zinc omadine. The Emery 644 was generally equal to or 2-fold superior in potency to Emersol 315 when tested against gram positive organisms. All gram positive bacteria tested were inhibited by the 1:50 dilution of the original hydrolysate. Emery 644 was also more active than Emersol 315 versus gram negative bacilli (4- to >8-fold) and *Candida albicans*. All Emery 644 MICs were <4%, or a 1:25 dilution of the provided full-strength hydrolysate.

When the antiseptic formulations of 2.5% zinc omadine and 3.0% fatty acids in n-propyl alcohol with and without Klucel were tested as a dilution of the final concentration, excellent inhibition was observed. All gram positive and gram negative organisms were inhibited at <0.12% (1:800 dilution) and <1% (<1:100 dilution), respectively. Vaginosis-associated organisms were effective at <0.025% (<1:400 dilution), and fungi at <1% (<1:100 dilution).

To assess the effect of blood on the antimicrobial activity of the antiseptic solution consisting of 2.5% zinc omadine and 3.0% fatty acids in n-propyl alcohol plus Klucel, the NCCLS procedure was performed using Mueller Hinton agar plates with and without 5% sheep blood. Antimicrobial activity was measured as the concentration inhibiting 50% of the tested organisms. As shown in Table VI, comparisons of MICs for the antiseptic with Klucel determined on media with and without 5% sheep erythrocytes failed to demonstrate any significant differences. Small amounts of blood appear to not affect the potency of fatty acids or zinc omadine.

TABLE VI

EFFECTS OF 5% SHEEP BLOOD ON THE AGAR DILUTION MICs OF THE ANTISEPTIC SOLUTION PLUS KLUCEL

| | MIC as a % Antiseptic Solution | |
|---|---|---|
| Organism | Agar + 5% Sheep[a] | Agar Alone |
| *C. albicans* (8501) | 0.008 | 0.015 |
| *E. coli* (25922) | 0.015 | 0.015 |
| *E. faecalis* (00049) | 0.015 | 0.015 |

TABLE VI-continued

EFFECTS OF 5% SHEEP BLOOD ON THE AGAR DILUTION MICs OF THE ANTISEPTIC SOLUTION PLUS KLUCEL

| | MIC as a % Antiseptic Solution | |
|---|---|---|
| Organism | Agar + 5% Sheep[a] | Agar Alone |
| *P. aeruginosa* (27853) | 0.25 | 0.25 |
| *S. aureus* (29213) | 0.03 | 0.03 |
| *S. aureus* (25923) | 0.03 | 0.03 |

[a]Agar supplemented with 5% sheep blood.

EXAMPLE 4

Preparation of Health Care Personnel Hand Wash and Exemplary Measurement of Anti Microbial Activity Threreof Five formulations of health care personnel hand wash antiseptic were prepared according to the procedure given in Example 2 by combining the ingredients given below in Table VII, adjusting the pH to 3.00–3.50 with either phosphoric acid, Dequest 2010 or citric acid, and q.s. to 100% with deionized water. The final concentrations are indicated either as percent (v/v) or percent (w/v).

A test was performed utilizing Formulation #5 outlined in Table VII, according to the Food and Drug Administration guidelines for approval of a health-care personnel handwash agent. *Federal Register* 59:31448–31450(Jun. 17, 1994). The test consists of ten cycles of contamination with a contaminating suspension of *Serratia marcescens* ATCC 14756 (American Type Culture Collection, Rockville, Md.) at $6 \times 10^8$ colony-forming units per milliliter (cfu/ml) followed by a wash with the test product and subsequent culturing after the first contamination, first wash, fifth wash and tenth wash. The object of the test is to reduce the number of contaminating transient microorganisms on the hands of health care personnel as much as possible without producing a deleterious effect on the hands of the user.

TABLE VII

EXEMPLARY FORMULATIONS OF HEALTH-CARE PERSONNEL HAND WASH

| | CONCENTRATION[a, b] FORMULATION NUMBER | | | | |
|---|---|---|---|---|---|
| COMPONENTS | 1 | 2 | 3 | 4 | 5 |
| ALCOHOL | | | | | |
| N-Propanol[a] | 70 | — | — | — | 70 |
| Isopropyl[a] | — | 70 | — | — | — |
| Ethyl[a] | — | — | 70 | — | — |
| Mixtures | | | | | |
| N-Propanol[a] | — | — | — | 50 | — |
| Isopropyl[a] | — | — | — | 20 | — |
| FATTY ACIDS | | | | | |
| Emery 305[b] | 2 | 2 | 2 | 2 | — |
| Emery 644[b] | — | — | — | — | 1 |
| Glycerol monolaurate[b] | — | — | — | — | 1.5 |
| Polymers of fatty acids[b] | 2 | 1 | — | 4 | — |
| DETERGENTS | | | | | |
| Dodecylammonium chloride[b] | 2 | 1 | 2 | 1 | — |
| Hyamine 1622[b] | 1 | 2 | 1 | 2 | — |
| THICKENING AGENT | | | | | |
| Klucel[b] HFNF (1500–3000) | 0.5 | 0.5 | 0.5 | 0.5 | 0.4 |
| SCENTS | | | | | |
| Phenylethyl alcohol[b] | 0.25 | 0.25 | 0.25 | 0.25 | 2 |
| Alpine scent[b] | 0.25 | — | 0.25 | — | — |
| Baby powder scent[b] | — | 0.25 | — | 0.25 | — |
| PRESERVATIVE | | | | | |
| Zinc omadine[b, c] | 0.1 | 0.1 | 0.1 | 0.1 | — |
| Liquipar oil[b] | 0.1 | 0.1 | 0.1 | 0.1 | 0.8 |
| ANTIOXIDANT | | | | | |
| Tenox PG[b] | — | — | — | — | 0.1 |
| Alpha tocopherol[b, d] | — | — | — | — | 0.1 |
| EMULSIFIER | | | | | |
| Polawax[b] | 6 | — | 6 | — | — |
| Arlacel[b] | — | 3 | — | 3 | — |

[a]Concentration in percent (v/v).
[b]Concentration in percent (w/v).
[c]48% suspension.
[d]5IU/0.1 ml In the antiseptic wash procedure, three milliliters of the novel antiseptic was placed in the palm of one hand, and the antiseptic was then rubbed onto all surfaces of the hands, including the interdigital spaces. Since the antiseptic formulations tested air-dry in approximately 45 seconds, no rinsing with water was required or desirable. After the hands were held in the air for approximately ten minutes, separate cultures were obtained from the right and left hands according to a modified "glove juice method." Loose fitting gloves were placed over the right and left hand, and 50 to 100 ml of sterile sampling solution (0.4 g potassium phosphate, monobasic, 10.1 g sodium phosphate, dibasic, and 1 g Triton X-100 per liter distilled water with pH adjusted to 7.8) was added to each glove. All surfaces of the hand, especially areas around fingernails, were massaged for one minute. An aliquot of the sampling solution in each glove was then cultured for *Serratia marcescens* using standard microbiological techniques, and the changes in microbial count from baseline were obtained.

Results from the health care hand wash tests are given in Table VIII, where the data represent absolute colony counts. The baseline was a grand average of the three subjects and was $1 \times 10^6$ cfu/ml. Excellent antimicrobial action was indicated by a reduction in microbial count ranging from about $1 \times 10^6$ to about 60 cfu/ml after the first wash, to about 12.5 cfu/ml after the fifth wash, and to about 0 cfu/ml after the tenth wash.

TABLE VIII

ANTIMICROBIAL ACTION OF HEALTH CARE PERSONNEL HAND WASH ANTISEPTICS

| | First Wash | | Fifth Wash | | Tenth Wash | |
|---|---|---|---|---|---|---|
| Subject | Left | Right | Left | Right | Left | Right |
| A | 18 | 0 | 0 | 0 | 0 | 0 |
| B | 0 | 18 | 0 | 0 | 0 | 0 |
| C | 131 | 18 | 75 | 0 | 0 | 0 |

EXAMPLE 5

Preparation of Surgical Hand Scrub

To provide stronger cleansing action and deeper penetration of the antiseptic action preferred in pre-operative hand scrubbing, four formulations of surgical hand scrubs were prepared by combining the ingredients given below in Table IX, adjusting the pH to 3.00–3.50 with phosphoric acid, and q.s. to 100% with deionized water. The final concentrations are indicated either as percent (v/v) or percent (w/v).

EXAMPLE 6

Quantitative Skin Degerming Evaluation using Enhanced Skin Flora

Prior to surgery or any invasive procedure, the skin is initially prepped with antimicrobial products to reduce the quantity of microorganisms on the skin in order to prevent infections. This study was performed to study the effect of the novel antiseptic in its ability to reduce the flora of the skin as compared to a control site.

TABLE IX

EXEMPLARY FORMULATIONS OF SURGICAL HAND SCRUB

| | CONCENTRATION[a,b] FORMULATION NUMBER | | | |
|---|---|---|---|---|
| COMPONENTS | 1 | 2 | 3 | 4 |
| ALCOHOLS | | | | |
| N-Propanol[a] | 62 | — | — | — |
| Isopropyl[a] | — | 70 | — | — |
| Mixtures | | | | |
| (1) N-Propanol[a] | — | — | 50 | — |
| + Isopropyl[a] | — | — | 20 | — |
| (2) N-Propanol[b] | — | — | — | 40 |
| + Ethyl[a] | — | — | — | 30 |
| EMULSIFIER | | | | |
| Polawax A31[b] | 4 | — | 4 | — |
| Arlacel 165[b] | — | 4 | — | 4 |
| DETERGENT | | | | |
| Dodecylammonium chloride[b,c] | 25 | — | — | — |
| Amine oxide[b] | — | 10 | — | — |
| Cetylpyridium chloride[b] | — | — | 10 | — |
| Hyamine 1622[b] | — | — | — | 10 |

TABLE IX-continued

EXEMPLARY FORMULATIONS OF SURGICAL HAND SCRUB

| COMPONENTS | CONCENTRATION[a,b] FORMULATION NUMBER | | | |
|---|---|---|---|---|
| | 1 | 2 | 3 | 4 |
| Mixtures | | | | |
| Laurylamine oxide[b] | — | — | 5 | 5 |
| Dodecylammonium chloride[b] | — | 10 | 5 | 5 |
| THICKENING AGENT | | | | |
| Klucel[b] HFNF (1500–3000) | 1 | 1 | 1 | 1 |
| SCENTS | | | | |
| Phenylethyl alcohol[b] | 0.25 | 0.25 | 0.25 | 0.25 |
| Alpine[b] | 0.25 | — | — | — |
| Other[b] | — | 0.25 | 0.25 | 0.25 |
| PRESERVATIVE | | | | |
| Zinc omadine[b,d] | 2 | 1 | 2 | 1 |
| Liquipar oil[b] | 1 | 1 | 1 | 1 |
| ANTIOXIDANT | | | | |
| Tenox Pg[b] | 0.10 | — | 0.10 | — |
| Tenox S1[b] | — | 0.10 | — | 0.10 |

[a]Concentration in percent (v/v).
[b]Concentration in percent (w/v).
[c]Hydro-alcoholic concentrate.
[d]48% suspension.

The Scrub formulation was prepared according to the procedure in Example 2, using the formulation in Table X, adjusting to pH 2.5±0.5 with phosphoric acid, and q.s. to 100% with distilled water.

The Omadine cream was prepared according to the formulation in Table XI given in %(w/v), by melting the oil ingredients together at 40° C., adding the water phase ingredients to the oils while mixing, rewarming to 40° C., q.s. to 100% with distilled water, and allowing the mixture to congeal.

TABLE X

FORMULATION FOR SURGICAL PREOPERATIVE ANTISEPTIC

| COMPONENTS | CONCENTRATION[a,b] |
|---|---|
| N-Propanol[a] | 70 |
| Iodine crystals (I$_2$)[b] | 2 |
| Emery 644[b] | 1 |
| Klucel[b] | 1 |
| Tenox PG[b] | 0.2 |
| Sodium EDTA[b] | 0.05 |
| Glycerine[b] | 2 |

[a]Concentration in percent (v/v).
[b]Concentration in percent (w/v).

TABLE XI

FORMULATION FOR OMADINE CREAM SURGICAL PREOPERATIVE ANTISEPTIC

| COMPONENTS | CONCENTRATION[a] |
|---|---|
| OIL PHASE | |
| Stearyl alcohol[a] | 4.53 |
| Cetyl alcohol[a] | 5.43 |
| White petrolatum[a] | 12.0 |
| Mineral oil[a] | 18.0 |

TABLE XI-continued

FORMULATION FOR OMADINE CREAM SURGICAL PREOPERATIVE ANTISEPTIC

| COMPONENTS | CONCENTRATION[a] |
|---|---|
| WATER PHASE | |
| Tween 80[a] | 4.5 |
| Sorbitol monolaurate[a] | 2.0 |
| Glycerine[a] | 2.0 |
| Aloe 10X[a] | 2.0 |
| Zinc omadine[a] | 1.5 |

[a]Concentration in percent (w/v).

Following a minimum 6 day wash-out period, the backs of each of the volunteers were occluded with Saran Wrap and anchored with Leukosilk Dressing. Approximately forty-eight hours after occlusion the Saran Wrap was removed. The skin was allowed to air dry. Then using a sterile template a grid was marked on the back with a sterile skin marker.

The Scrub Formulation was applied with a quarter of a sterile surgical sponge brush. The brush was immersed in the scrub solution and applied by rubbing the solution into the designated test area. The scrubbing with the brush continued for approximately 90 seconds, squeezing the brush as necessary to always assure that there was a generous amount of antiseptic present on the test site. After ninety-seconds, the brush was reimmersed in the solution and reapplied for another ninety-seconds. The scrub solution was applied for a total of 3.0 minutes. After the second application the test site was allowed to completely dry by allowing the alcohol to evaporate.

The Omadine Cream was applied and rubbed into the skin for one minute by hand with the applicant wearing sterile gloves. The cream contained 1.5% Omadine. Approximately five grams was applied to each test site.

Cultures were obtained using the quantitative culture scrub technique of Williams and Kligman, using a sterile scrubbing cup (5.07 cm$^2$, internal area) containing appropriate neutralizer sampling solution. Three milliliters of sampling solution were pipetted in and the area scrubbed with moderate pressure for one minute using a sterile Teflon "policeman". The fluid is aspirated, replaced with 3 ml of fresh solution, and the scrub was repeated. Cultures were obtained in this fashion at baseline, and at the following post-scrub times: ten minutes, six hours, and twenty-four hours.

Results of this study are presented in Tables XII–XIV. Both antiseptic treatments provided reduction in microbial count as opposed to the control count. The alcohol-iodine antiseptic showed highly significant reduction within ten minutes of application and maintained the reduction over 24 hours, illustrating excellent quick-kill and persistence even in the absence of bispyrithione. The Zinc Omadine antiseptic showed some decrease in microbial count at 10 minutes and indicated significant reduction over time.

TABLE XII

ALCOHOL ANTISEPTIC POST-TREATMENT MICROBIAL COUNT (LOG BASE 10 COUNTS/CM$^2$)

| Subject No. | Baseline | 10 min. | 6 Hours | 24 Hours |
|---|---|---|---|---|
| #1 | 5.982271 | 0.3802 | 0.38021 | 1.23045 |
| #2 | 5.857332 | 0.3802 | 0.38021 | 0.07918 |
| #3 | 5.301030 | 0.0792 | 0.07918 | 0.07918 |
| #4 | 6.079181 | 1.5051 | 0.07918 | 0.38021 |
| #5 | 5.079181 | 1.6127 | 1.98677 | 1.81291 |
| #6 | 5.612784 | — | 0.07918 | 0.07918 |
| Mean | 5.651963 | 0.6596 | 0.6433 | 0.61018 |
| Log Reduction | — | 4.9923 | 5.0086 | 5.04177 |

TABLE XIII

ZINC OMADINE POST-TREATMENT MICROBIAL COUNT (LOG BASE 10 COUNTS/CM$^2$)

| Subject No. | Baseline | 10 min. | 6 Hours | 24 Hours |
|---|---|---|---|---|
| #1 | 5.653213 | 5.6627 | 4.17609 | 2.98227 |
| #2 | 5.447158 | 5.7482 | 4.04139 | 2.81291 |
| #3 | 5.653212 | 5.0515 | 2.89763 | 3.07918 |
| #4 | 5.14973 | 4.7993 | 3.79239 | 3.07918 |
| #5 | 5.991226 | 5.7160 | 3,60206 | 3.62758 |
| #6 | 5.380211 | 4.8388 | 4.23044 | 3.14613 |
| Mean | 5.589999 | 5.3783 | 3.79000 | 3.12707 |
| Log Reduction | — | 0.21161 | 1.79999 | 2.46293 |

TABLE XIV

CONTROL AREA POST-TREATMENT MICROBIAL COUNT (LOG BASE 10 COUNTS/CM$^2$)

| Subject No. | Baseline | 10 min. | 6 Hours | 24 Hours |
|---|---|---|---|---|
| #1 | 5.39794 | 5.9867 | 5.11394 | 5.04139 |
| #2 | 5.778151 | 5.8750 | 5.11394 | 5.07918 |
| #3 | 5.838849 | 5.7076 | 5.07918 | 5.14613 |
| #4 | 5.477121 | 6.5682 | 4.77085 | 4.94448 |
| #5 | 5.724276 | 6.2304 | 5.14612 | 5.56820 |
| #6 | 4.556303 | 4.9031 | 5.56820 | 4.61278 |
| Mean | 5.462107 | 5.8785 | 5.13204 | 5.065362 |
| Log Reduction | — | 0.4164 | 0.33065 | 0.396745 |

EXAMPLE 7

Formulation of Preoperative Antiseptic and Evaluation of Treatment

Six formulations of preoperative antiseptics were prepared according to the procedure given in Example 2 by combining the ingredients given below in Table XV, adjusting the pH to 3.00–4.00 with phosphoric acid, and q.s. to 100 ml with deionized water. The final concentrations are indicated either as percent (v/v) or percent (w/v).

The antimicrobial action of the antiseptic Formulation #6 was compared to that of a soap and water scrub, and an Iodophor (Betadine) scrub, using the FDA patient preoperative skin preparation protocol which specifies the abdomen and groin crease as the test sites. (*Federal Register* 59:31450–31452 (Jun. 17, 1994)). One contralateral side of the abdomen or groin crease is used as the test site and the other side was used as the baseline control site. Samples were taken at baseline and then at 10 minutes, 6 hours, and 24 hours posttreatment, using the scrubbing cup technique described in Example 6. The scrub time for the antiseptic Scrub formulation and soap and water was three minutes, and the Iodophor was five minutes.

The results from the comparative study (Table XVI–XXII) show that at all time points, the antimicrobial action of the antiseptic was higher than with soap and water, and with iodophor. At ten minutes posttreatment with the antiseptic, there was 59–100% drop in organism count for the abdomen and 87–100% drop for the groin crease, demonstrating very effective quick-kill.

TABLE XV

FORMULATIONS OF PREOPERATIVE ANTISEPTICS

| COMPONENTS | CONCENTRATION[a,b] FORMULATION NUMBER | | | | | |
|---|---|---|---|---|---|---|
| | 1 | 2 | 3 | 4 | 5 | 6 |
| ALCOHOL | | | | | | |
| N-Propanol[a] | 67 | — | — | — | — | 70 |
| Isopropyl Alcohol[a] | — | 70 | — | — | — | — |
| Ethyl Alcohol[a] | — | — | 70 | — | — | — |
| Mixtures | | | | | | |
| N-Propanol[a] + | — | — | — | 40 | — | — |
| Isopropyl[a] | — | — | — | 30 | — | — |
| N-Propanol[a] + | — | — | — | — | 50 | — |
| Amyl[a] | — | — | — | — | 17 | — |
| PROPYLENE GLYCOL[a] | 5 | — | — | — | — | — |
| EMULSIFIER | | | | | | |
| Polawax[b] | 6 | 6 | 6 | 6 | 6 | 6 |
| FATTY ACIDS | | | | | | |
| Emery 644[b] | 2 | — | 2 | — | 2 | 2 |
| Emery 305[b] | — | 2 | — | 2 | — | — |
| NITROGEN COMPOUND | | | | | | |
| Dodecylammonium chloride[b,c] | 4 | — | — | — | 4 | — |
| Hyamine 1622[b] | — | 2 | — | — | — | 2 |
| Laurylamine oxide[b] | — | — | 2 | — | — | — |
| Cetylpyridium chloride[b] | — | — | — | 2 | — | — |
| OTHER QUICK-KILL AGENT | | | | | | |
| Chlorhexidine[b] | — | 1 | — | — | — | — |
| Triclosan[b] | — | — | 1 | — | — | — |
| PCMX[b,e] | — | — | — | 1 | — | — |
| Iodine[b] + | — | — | — | — | 2 | — |
| Sodium iodide[b] | — | — | — | — | 4 | — |
| PRESERVATIVE | | | | | | |
| Zinc Omadine[b,d] | 2 | 2 | 2 | 2 | — | 2 |
| AROMATIC ALCOHOL | | | | | | |
| Phenylethyl alcohol[b] | 0.25 | — | 0.25 | — | 0.25 | 0.25 |
| Benzyl alcohol[b] | — | 4 | — | 4 | — | — |
| ANTIOXIDANT | | | | | | |
| Tenox PG[b] | 0.1 | — | 0.1 | — | 0.1 | 0.1 |
| Tenox S1[b] | — | 0.1 | — | 0.1 | — | — |

[a]Concentration in percent (v/v).
[b]Concentration in percent (w/v).
[c]Hydro-alcoholic concentration.
[d]48% suspension.
[e]PCMX = para-chloro-meta-zylenol

TABLE XVI

LOG10 CHANGES IN COUNTS FROM BASELINE WITH THREE MINUTE SCRUB WITH ANTISEPTIC
SITE: ABDOMEN

| Subject | Baseline | 10 min | Log Drop | % Drop | 6 Hr | Log Drop | % Drop | 24 Hr | Log Drop | % Drop |
|---|---|---|---|---|---|---|---|---|---|---|
| A | 1.3324 | 0.0000 | 1.3324 | 100.00 | 0.0000 | 1.3324 | 100.00 | 0.0000 | 1.3324 | 100.00 |
| B | 2.9138 | 0.6021 | 2.3118 | 79.34 | 0.0000 | 2.9138 | 100.00 | 0.3979 | 2.5158 | 86.34 |
| C | DATA | NOT | DONE | | | | | | | |
| D | 1.6767 | 0.0000 | 1.6767 | 100.00 | −0.3010 | 1.9777 | 117.95 | −0.3010 | 1.9977 | 117.95 |
| E | 2.2695 | 0.0000 | 2.2695 | 100.00 | −0.3010 | 2.5705 | 113.26 | 0.0000 | 2.2695 | 100.00 |
| F | 1.8388 | 0.0000 | 1.8388 | 100.00 | 0.9777 | 0.8611 | 46.83 | 0.0000 | 1.8388 | 100.00 |
| G | 2.2455 | 0.9294 | 1.3161 | 58.61 | 0.0000 | 2.2455 | 100.00 | 0.0000 | 2.2455 | 100.00 |
| H | 1.2304 | 0.0000 | 1.2304 | 100.00 | 0.0000 | 1.2304 | 100.00 | −0.3010 | 1.5315 | 124.47 |
| MEAN | 1.9296 | 0.2187 | 1.7108 | 91.14 | 0.0537 | 1.8759 | 96.86 | −0.0292 | 1.9588 | 104.11 |

TABLE XVII

LOG10 CHANGES IN COUNTS FROM BASELINE WITH THREE MINUTE SCRUB WITH ANTISEPTIC
SITE: GROIN CREASE

| Subject | Baseline | 10 min. | Log Drop | % Drop | 6 Hr | Log Drop | % Drop | 24 Hr | Log Drop | % Drop |
|---|---|---|---|---|---|---|---|---|---|---|
| A | 4.2516 | 0.5441 | 3.7076 | 87.20 | 0.0000 | 4.2516 | 100.00 | 0.0000 | 4.2516 | 100.00 |
| B | 3.5740 | 0.0000 | 3.5740 | 100.00 | 0.0000 | 3.5740 | 100.00 | 1.8722 | 1.7019 | 47.62 |
| C | DATA | NOT | DONE | | | | | | | |
| D | 4.2214 | 0.0000 | 4.2214 | 100.00 | 1.6902 | 2.5312 | 59.96 | 2.0191 | 2.2023 | 52.17 |
| E | 2.6385 | 0.0000 | 2.6385 | 100.00 | 0.3010 | 2.3375 | 88.59 | 0.0000 | 2.6385 | 100.00 |
| F | 5.2292 | 0.0000 | 5.2292 | 100.00 | 1.0969 | 4.1323 | 79.02 | 0.3979 | 4.8312 | 92.39 |
| G | 3.6335 | 0.0000 | 3.6335 | 100.00 | 0.3010 | 3.3324 | 91.72 | 0.0000 | 3.6335 | 100.00 |
| H | 5.0394 | 0.0000 | 5.0394 | 100.00 | 0.8751 | 4.1644 | 82.64 | −0.3010 | 5.3404 | 105.97 |
| MEAN | 4.0840 | 0.0777 | 4.0062 | 98.17 | 0.6092 | 3.4748 | 85.99 | 0.5697 | 3.5142 | 85.45 |

TABLE XVIII

LOG10 CHANGES IN COUNTS FROM BASELINE WITH THREE MINUTE SCRUB WITH SOAP/WATER
SITE: ABDOMEN

| Subject | Baseline | 10 min | Log Drop | % Drop | 6 Hr | Log Drop | % Drop | 24 Hours | Log Drop | % Drop |
|---|---|---|---|---|---|---|---|---|---|---|
| A | 0.0000 | 0.5441 | −0.5441 | 00.00 | 0.0000 | 0.0000 | 00.00 | −0.3010 | 0.3010 | 00.00 |
| B | 1.4771 | 0.6021 | 0.8751 | 59.24 | 0.7782 | 0.6990 | 47.32 | 0.3010 | 1.1761 | 79.62 |
| C | DATA | NOT | DONE | | | | | | | |
| D | 2.1569 | 1.4914 | 0.6655 | 30.85 | 1.1761 | 0.9818 | 45.47 | 1.2175 | 0.9394 | 43.55 |
| E | 2.1106 | 0.6532 | 1.4574 | 69.05 | 0.8451 | 1.2655 | 59.96 | 1.4698 | 0.6408 | 30.36 |
| F | 2.1973 | 2.6532 | −0.4559 | −20.75 | 0.3010 | 1.8963 | 86.30 | 2.1383 | 0.0590 | 2.68 |
| G | 1.0607 | −0.3010 | 1.3617 | 128.38 | 0.4771 | 0.5836 | 55.02 | 0.0000 | 1.0607 | 100.00 |
| H | 3.9345 | 1.7443 | 2.1902 | 55.67 | 0.8751 | 3.0594 | 77.76 | 0.3979 | 3.5366 | 89.89 |
| MEAN | 1.8482 | 1.0553 | 0.7928 | 49.06 | 0.6361 | 1.2121 | 53.12 | 0.7462 | 1.1019 | 49.44 |

TABLE XX

LOG10 CHANGES IN COUNTS FROM BASELINE WITH THREE MINUTE SCRUB WITH SOAP/WATER
SITE: GROIN CREASE

| Subject | Baseline | 10 Min | Log Drop | % Drop | 6 Hours | Log Drop | % Drop | 24 Hours | Log Drop | % Drop |
|---|---|---|---|---|---|---|---|---|---|---|
| A | 0.0000 | 2.7482 | −2.7482 | 00.00 | 1.3010− | −1.3010 | 0.000 | 0.6990 | −0.6990 | 0.00 |
| B | 2.6284 | 2.7818 | −0.1534 | −05.83 | 2.6233 | 0.0051 | 0.200 | 2.1903 | 0.4381 | 16.67 |
| C | DATA | NOT | DONE | | | | | | | |
| D | 5.2055 | 5.0512 | 0.1543 | 02.96 | 3.7076 | 1.4979 | 28.78 | 3.8543 | 1.3512 | 25.96 |
| E | 3.1239 | 2.6181 | 0.5058 | 16.19 | 1.8751 | 1.2488 | 39.98 | 2.1903 | 0.9335 | 29.88 |

TABLE XX-continued

LOG10 CHANGES IN COUNTS FROM BASELINE WITH
THREE MINUTE SCRUB WITH SOAP/WATER
SITE: GROIN CREASE

| Subject | Baseline | 10 Min | Log Drop | % Drop | 6 Hours | Log Drop | % Drop | 24 Hours | Log Drop | % Drop |
|---|---|---|---|---|---|---|---|---|---|---|
| F | 5.1658 | 4.3493 | 0.8166 | 15.81 | 4.3909 | 0.7749 | 15.00 | 3.9800 | 1.1858 | 22.97 |
| G | 4.2822 | 2.8325 | 1.4497 | 33.85 | 2.6284 | 1.6538 | 36.62 | 1.3010 | 2.9811 | 69.62 |
| H | 4.5447 | 1.2787 | 3.2659 | 71.86 | 2.8692 | 1.6755 | 36.87 | 1.8451 | 2.6996 | 59.40 |
| MEAN | 3.5643 | 3.0942 | 0.4701 | 19.26 | 2.7708 | 0.7936 | 22.78 | 2.2943 | 1.2701 | 32.07 |

TABLE XXI

LOG10 CHANGES IN COUNTS FROM BASELINE WITH
FIVE MINUTE SCRUB WITH IODOPHOR
SITE: ABDOMEN

| Subject | Baseline | 10 Min | Log Drop | % Drop | 6 Hours | Log Drop | % Drop | 24 Hours | Log Drop | % Drop |
|---|---|---|---|---|---|---|---|---|---|---|
| I | 0.9031 | 0.0000 | 0.9031 | 100.00 | 1.6021 | −0.6990 | −77.40 | 0.0000 | 0.9031 | 100.0 |
| J | 1.0792 | 0.1761 | 0.9031 | 83.68 | 0.0000 | 1.0792 | 100.00 | 1.1761 | −0.0969 | −8.98 |
| K | 2.6335 | 2.0128 | 0.6206 | 23.57 | 2.3222 | 0.3113 | 11.62 | 1.5882 | 1.0065 | 40.45 |
| L | 1.3979 | 0.7404 | 0.6577 | 47.04 | 1.6532 | −0.2553 | −18.26 | 0.0000 | 1.3979 | 100.00 |
| M | 1.3324 | 2.7076 | −1.3751 | −103.20 | 0.6690 | 0.6335 | 47.54 | 1.3010 | 0.0314 | 2.35 |
| N | DATA | NOT | DONE | | | | | | | |
| O | 2.4624 | 1.1761 | 1.2863 | 52.24 | 2.5682 | −0.1058 | −4.30 | 1.8451 | 0.6173 | 25.07 |
| P | DATA | NOT | DONE | | | | | | | |
| MEAN | 1.6348 | 1.1355 | 0.4993 | 33.89 | 1.4741 | 0.1606 | 9.90 | 0.9817 | 0.6530 | 43.15 |

TABLE XXII

LOG10 CHANGES IN COUNTS FROM BASELINE WITH
FIVE MINUTE SCRUB WITH IODOPHOR
SITE: GROIN CREASE

| Subject | Baseline | 10 Min. | Log Drop | % Drop | 6 Hours | Log Drop | % Drop | 24 Hours | Log Drop | % Drop |
|---|---|---|---|---|---|---|---|---|---|---|
| I | 5.4166 | 4.3086 | 1.1081 | 20.46 | 1.5441 | 3.8726 | 71.49 | 0.0000 | 5.4166 | 100.00 |
| J | 3.1055 | 1.0212 | 2.0843 | 67.12 | 1.3979 | 1.7076 | 54.99 | 1.5441 | 1.5614 | 50.28 |
| K | 5.6154 | 3.9978 | 1.6178 | 28.81 | 2.7672 | 2.8483 | 50.72 | 2.6233 | 2.9922 | 53.28 |
| L | 3.2122 | 0.0000 | 3.2122 | 100.00 | 3.3365 | −0.1243 | −3.87 | 1.1761 | 2.0361 | 63.39 |
| M | 3.2765 | 3.1207 | 0.1559 | 4.76 | 2.1903 | 1.0861 | 33.15 | 1.0000 | 2.2765 | 59.48 |
| N | DATA | NOT | DONE | | | | | | | |
| O | 5.0683 | 3.4914 | 1.5750 | 31.09 | 3.1156 | 1.9507 | 38.50 | 3.7443 | 1.3220 | 28.09 |
| P | DATA | NOT | DONE | | | | | | | |
| MEAN | 4.2821 | 2.6566 | 1.6255 | 42.04 | 2.3919 | 1.8912 | 42.83 | 1.6813 | 1.6008 | 60.42 |

Overall, 48–100% drop in organism counts were maintained through twenty-four hours posttreatment with the antiseptic which reveals fast acting antimicrobial activity and persistence lasting for twenty-four hours with a single application.

EXAMPLE 8

Preparation of Acne Treatment Antiseptic and Evaluation of Acne Treatment

Cream formulations of the antiseptic solution given in Table XXIII and XXIV were prepared according to the following procedure. Water and water soluble ingredients were combined and heated to 75–80° C. with agitation. The lipids and lipid soluble ingredients were combined and heated to 75° C. with agitation. The water soluble portion and the lipid soluble portion were combined and cooled to 50° C. with agitation. A buffer and preservative were added followed by q.s. to 100 ml with deionized water, and the resulting cream was cooled to 25° C. with agitation. In formulas that contain zinc omadine, the cream was cooled before adding the zinc omadine.

Three hundred patients with acne were referred to a board certified dermatologist for treatment with Formulation #5 in Table XXIII for patients suffering from inflammatory, papular, and papulopustular acne and with the formulation in Table XXIV, for cystic acne. All of these patients had failed oral antibiotic therapy for acne. The patients with inflammatory, papular and papulopustular had dramatic improvement with resolution of their acne in 50% of the cases and great improvement in 25% of the cases. Approximately 25% of the cases only had mild improvement. In patients showing only mild improvement, Retin A was added to their treatment regimen for two weeks with resolution of their recalcitrant acne. Retin A was used at bedtime, and the acne antiseptic cream was used in the morning on patients suffering from primary follicular obstruction. After about two weeks of this combination therapy the patients were able to stop Retin A but continue the acne cream to control of their acne. The acne antiseptic cream helped reduce the inflammatory response normally seen with Retin A.

TABLE XXIII

EXEMPLARY FORMULATIONS OF THE ACNE CREAMS

| COMPONENTS | CONCENTRATION[a] FORMULATION NUMBER | | | | |
|---|---|---|---|---|---|
| | 1 | 2 | 3 | 4 | 5 |
| OILS | | | | | |
| Emersol 305[a] | 5 | 10 | 5 | 10 | 2 |
| Mineral oil[a] | 5 | — | — | — | 10 |
| Safflower oil[a] | 5 | 5 | 5 | — | — |
| Wheat germ oil[a] | 3 | 3 | 3 | 8 | — |
| Stearyl alcohol[a] | — | — | — | — | 5.5 |
| Cetyl alcohol[a] | — | — | — | — | 4.7 |
| EMULSIFIER | | | | | |
| Polawax[a] | 10 | 10 | 10 | 10 | — |
| Sodium lauryl sulfate[a] | — | — | — | — | 1.5 |
| PENETRATION INHIBITOR | | | | | |
| White petrolatum[a] | 10 | 10 | 10 | 10 | 12.5 |
| ANTIOXIDANT | | | | | |
| Tenox S1[a] | 10 | 10 | 10 | 10 | 5 |
| + Propylene glycol[b] | 7 | 7 | 7 | 7 | — |
| + Propyl gallate[a] | 2 | 2 | 2 | 2 | — |
| + Citric acid[a] | 1 | 1 | 1 | 1 | — |
| PRESERVATIVE | | | | | |
| Zinc omadine[a,c] | 1.5 | 1.5 | 1.5 | 1.5 | 1.5 |
| KERATOLYTIC AGENT | | | | | |
| Salicylic acid[a] | 0.5 | — | — | — | — |
| Resorcinol[a] | — | 5 | — | 3 | — |
| Resorcinol monoacetate[a] | — | — | 5 | — | — |
| Sulfur[a] | — | — | — | 3 | — |
| ANTIBIOTIC | | | | | |
| Erythromycin[a] | — | 2 | — | — | — |
| Clindamycin[a] | — | — | 2 | — | — |
| Tetracycline[a] | — | — | — | 2 | — |

[a]Concentration in weight percent (w/v).
[b]Inhibits penetration beyond the basal cell layer.
[c]48% suspension.

For treatment of cystic acne, the dermatologist's impression was that the formulation given in Table XXIV was better than the prescription medication benzamycin (a combination of erythromycin and benzoyl peroxide in a alcohol base).

TABLE XXIV

EXEMPLARY FORMULATIONS OF CYSTIC ACNE FORMULAE

| COMPONENTS | CONCENTRATION[a,b] |
|---|---|
| ALCOHOL | |
| Decanol[a] | 2% |
| FATTY ACIDS | |
| Emersol 305[b] | 2% |
| PRESERVATIVE | |
| Zinc omadine[b] | |
| PENETRATING AGENT | |
| Propylene glycol[a] | 10% |
| ANTIOXIDANT | |
| Propyl gallate[b] | 1% |
| ADDITIONAL ADDITIVES | |
| Progesterone[b] | 0.50% |
| Aldactone[b] | 1% |

[a]Concentration in volume percent (v/v).
[b]Concentration in weight percent (w/v).
[c]The above ingredients may be mixed with short-chain alkyl alcohols or mixed in a cream base without medium-chain alcohols which could inhibit penetration.

In the treatment of acne there did not seem to be any difference in response to where the patient was afflicted, i.e., face, anterior chest or back. The incidence of side-effects were less than one percent and restricted to a mild stinging sensation initially when the cream was applied. In patients only receiving the novel acne formulation the patients were instructed to rub in a small amount of cream to the face prior to bedtime, i.e., once a day treatment.

The same formula can be used to treat seborrhea, onychomycosis, and athlete's foot.

EXAMPLE 9

Treatment of Acne Rosacea with Acne Cream

Ten patients with acne rosacea resistant to improvement with metronidazole cream and antibiotics were treated with Formulation #5 in Table XXIII. All patients had complete resolution of the inflammation of acne rosacea. All patients were able to discontinue their metronidazole and antibiotics. If Emery 644 was substituted for Emersol 305, all of the patients became much worse. If the patient discontinued the acne rosacea cream, they had recrudescence of their acne rosacea after about seven to ten days. When the acne rosacea cream was reapplied once a day at bedtime there was again complete healing of their acne rosacea in about seven to fourteen days.

EXAMPLE 10

Preparation of Wound and Burn Care Antiseptic and Evaluation of Treatment

Wound and burn care antiseptic formulae were prepared according to the procedure in Example 2, using the formulation in Table XXIV, q.s. to 100% with propylene glycol.

TABLE XXIV

FORMULATION OF WOUND AND BURN CARE ANTISEPTIC

| COMPONENTS | CONCENTRATION |
|---|---|
| FATTY ACID | |
| Emery 305 | 4.00 ml |
| PRESERVATIVE | |
| Propionic acid | 4.00 ml |
| Omadine disulfide | 0.10 grams |
| pH ADJUSTING AGENT | |
| Dequest 2010 | 1.00 ml |
| THICKENING AGENT | |
| Klucel | 0.50 grams |
| ADDITIONAL INGREDIENTS | |
| Lidocaine | 2.00 grams |
| Hyaluronic acid (Sodium Salt) | 120 µg/ml |

Four patients with peri-rectal lesions that failed to heal for three months to three years following either total colectomy or pilo-nidal cyst surgery were treated with the wound care formulation twice a day. The patients soaked the antiseptic formulation in sterile gauze and packed the area twice a day. All patients had complete healing of their infected abscesses within ten to fourteen days.

One patient was treated with the wound care formula for second and third degree burns of the face, shoulder, side and thigh. Sterile gauze was saturated with the antiseptic formula and wrapped over the area two to three times a day. The burns healed completely without infection or scar formation.

EXAMPLE 11

Preparation of Antiseptic Eye Treatment And Evaluation of Treatment

Antiseptic eye treatment was prepared according to the procedure in Example 1, using the formulation in Table XXV.

TABLE XXV

EXEMPLARY FORMULATIONS OF ANTISEPTIC EYE TREATMENT

| COMPONENTS | CONCENTRATION[a,b] |
|---|---|
| PROPYLENE GLYCOL[a] | 85% |
| FATTY ACIDS | |
| Propionic acid[b] | 5% |
| Emery 658[b] | 0.1% |
| Emery 305[b] | 0.1% |
| PRESERVATIVE | |
| Omadine salt[b] | 0.1% |
| ADDITIONAL INGREDIENTS | |
| Sodium EDTA[b] | 1.0% |
| Deionized water[a] | 6.7% |
| Electrolytes[c] | |

TABLE XXV-continued

EXEMPLARY FORMULATIONS OF ANTISEPTIC EYE TREATMENT

| COMPONENTS | CONCENTRATION[a,b] |
|---|---|
| OPTIONAL INGREDIENT | |
| Zinc sulfate[b] | 1.0% |

[a]Concentration in percent volume (v/v).
[b]Concentration in weight percent (w/v).
[c]Concentration of electrolytes to make formulation isotonic and to buffer to pH 5.0

The treatment of both bacterial and viral eye infections has been accomplished using 5% propionic acid, 1%–5% zinc sulfate, and with either Omadine MDS or Omadine DS at 0.1% as the preservative. This formulation is applied every four hours with rapid resolution of both viral or bacterial eye infections.

EXAMPLE 12

Preparation of Antiseptic Cream

Antibiotic creams were prepared according to the procedure in Example 8, using the formulations in Table XXVI.

EXAMPLE 13

Prepatation of Mucous Membrane Antiseptic

Mucous membrane antiseptics were prepared according to the procedure in Example 2, using the formulations in Table XXVII, adjusting the pH to 4 and q.s. to 100 ml with deionized water.

EXAMPLE 14

Preparation of Burn Treatment

Antiseptic for burn treatment was prepared by combining linoleic acid with or without silver sulfadiazine, and phenethylamine (PEA) in a cream vehicle or lotion.

TABLE XXVI

EXEMPLARY FORMULATIONS OF ANTIBIOTIC CREAM

| | CONCENTRATION[a] FORMULATION NUMBER | | | |
|---|---|---|---|---|
| COMPONENTS | 1 | 2 | 3 | 4 |
| OILS | | | | |
| Mineral oil | 5 | — | — | — |
| Safflower oil | 5 | 5 | 5 | — |
| Wheat germ oil | 3 | 3 | 3 | 8 |
| FATTY ACID | | | | |
| Emersol 305 | 5 | 10 | 5 | 10 |
| PENETRATION INHIBITOR[b] | | | | |
| White petrolatum | 10 | 10 | 10 | 10 |
| EMULSIFIER | | | | |
| Polawax | 10 | — | 10 | — |
| Glyceryl monostearate | — | 2 | — | 2 |
| ANTIOXIDANT | | | | |
| Tenox S1 | 10 | 10 | 10 | 10 |
| Tenox PG | 2 | 2 | 2 | 2 |

TABLE XXVI-continued

EXEMPLARY FORMULATIONS OF ANTIBIOTIC CREAM

| COMPONENTS | CONCENTRATION[a] FORMULATION NUMBER | | | |
|---|---|---|---|---|
| | 1 | 2 | 3 | 4 |
| PRESERVATIVE | | | | |
| Zinc omadine[c] | 1.5 | 1.5 | 1.5 | 1.5 |
| ANTIBIOTICS | | | | |
| Neosporin | 1 | — | — | — |
| Chloramphenicol | — | 1 | — | — |
| Tetracycline | — | — | 2 | — |
| Gentamicin | — | — | — | 1 |
| DEIONIZED WATER | q.s. to 100 ml | | | |

[a]Concentration in weight percent (w/v).
[b]Inhibits penetration beyond basal cell layer.
[c]48% suspension.

TABLE XXVII

EXEMPLARY FORMULATIONS OF MUCOUS MEMBRANE ANTISEPTIC

| COMPONENTS | CONCENTRATION[a,b] FORMULATION NUMBER | | | | |
|---|---|---|---|---|---|
| | 1 | 2 | 3 | 4 | 5 |
| PROPYLENE GLYCOL[a] | 60 | 60 | 60 | 60 | 60 |
| ANTIOXIDANT | | | | | |
| Tenox S1[b] | 10 | 10 | 10 | 10 | 10 |
| EMULSIFIER | | | | | |
| Polawax[b] | 6 | 6 | 6 | 6 | 6 |
| ANTIMICROBIAL FATTY ACIDS | | | | | |
| Emery 644[b] | 12 | — | 7 | — | 7 |
| Emery 305[b] | — | 10 | — | 2 | — |
| Glacial acetic acid[b] | 5 | — | — | 5 | 5 |
| Propionic acid[b] | — | 5 | 5 | — | — |
| Glycerol monolaurate[b] | — | — | — | — | 3 |
| Emery 658[b] | — | 5 | 1 | 4 | 2 |
| PERSISTENT AGENT PRESERVATIVE | | | | | |
| Zinc omadine[b,c] | 1 | 1 | 1 | 1 | 1 |
| THICKENING AGENT | | | | | |
| Klucel[b] HFNF - 1500–3000 | 0.5 | 0.5 | 0.5 | 0.5 | 0.5 |
| AROMATIC ALCOHOL | | | | | |
| Phenylethyl alcohol[b] | 1 | 1 | 1 | 1 | 1 |
| CHELATOR | | | | | |
| Dequest 2010 and 2060[b] | 1 | 1 | 1 | 1 | 1 |
| pH ADJUSTING AGENT[b] | | | | | |
| Sodium acetate or sodium propionate adjust pH to 4.0 | | | | | |

[a]Concentration in percent volume (v/v).
[b]Concentration in weight percent (w/v).
[c]48% suspension

I claim:

1. An antiseptic formulation for topical application to animal skin, comprising an antimicrobial alcohol selected from the group consisting of ethanol, isopropanol, n-propanol and mixtures thereof; an antimicrobial lipid selected from the group consisting of free fatty acids having from six to eighteen carbons, glycerol monolaurate and mixtures thereof; and zinc pyrithione.

2. The antiseptic formulation of claim 1, wherein said antimicrobial lipid is a mixture of free fatty acids having sixteen to eighteen carbons.

3. The antiseptic formulation of claim 2, wherein said antimicrobial lipid is a mixture of unsaturated free fatty acids having sixteen to eighteen carbons.

4. The antiseptic formulation of claim 2, wherein said antimicrobial lipid is a mixture of linolenic acid, oleic acid, linoleic acid, palmitic acid, and stearic acid.

5. The antiseptic formulation of claim 1, wherein said antimicrobial lipid is a mixture of saturated free fatty acids having six to twelve carbons.

6. The antiseptic formulation of claim 5, wherein said antimicrobial lipid is caprylic acid.

7. The antiseptic formulation of claim 1, wherein said free fatty acids consist essentially of linolenic acid.

8. The antiseptic formulation of claim 1, wherein said free fatty acids consist essentially of linoleic acid.

9. The antiseptic formulation of claim 1, wherein said antimicrobial lipid is glycerol monolaurate.

10. The antiseptic formulation of claim 1, further comprising an agent effective to form a stable suspension or emulsion of said alcohol, said lipid, and said zinc pyrithione.

11. The antiseptic formulation of claim 10, wherein said formulation has an acidic pH.

12. The antiseptic formulation of claim 1, wherein said formulation has an acidic pH.

13. An antiseptic formulation for topical application to animal skin, comprising an antimicrobial alcohol selected from the group consisting of ethanol, isopropanol, n-propanol and mixtures thereof; and a bispyrithione salt.

14. The antiseptic formulation of claim 13, further comprising an agent effective to form a stable suspension or emulsion of said alcohol and said bispyrithione salt.

15. The antiseptic formulation of claim 14, wherein said bispyrithione salt is selected from the group consisting of zinc pyrithione, magnesium pyrithione and mixtures thereof.

16. The antiseptic formulation of claim 15, wherein said formulation has an acidic pH.

17. The antiseptic formulation of claim 14, wherein said formulation has an acidic pH.

18. The antiseptic formulation of claim 13, wherein said bispyrithione salt is selected from the group consisting of zinc pyrithione, magnesium pyrithione and mixtures thereof.

19. The antiseptic formulation of claim 18, wherein said formulation has an acidic pH.

20. The antiseptic formulation of claim 13, wherein said formulation has an acidic pH.

21. The antiseptic formulation of claim 2, 5, 3, 4, 7, 8, 6, or 9, further comprising an agent effective to form a stable suspension or emulsion of said alcohol, said lipid, and said zinc pyrithione.

22. The antiseptic formulation of claim 2, 5, 3, 4, 7, 8, 6, or 9, wherein said formulation has an acidic pH.

* * * * *